United States Patent [19]
Palermo et al.

[11] Patent Number: 5,965,554
[45] Date of Patent: Oct. 12, 1999

[54] ANTIPSYCHOTIC AGENTS, COMPOSITIONS AND METHOD OF USE

[75] Inventors: Mark G. Palermo, Netcong; Lawrence L. Martin, Lebanon; Peter A. Nemoto, Raritan, all of N.J.

[73] Assignee: Hoechst Marion Roussel, Inc., Bridgewater, N.J.

[21] Appl. No.: 09/150,971

[22] Filed: Sep. 11, 1998

Related U.S. Application Data

[62] Division of application No. 08/921,480, Sep. 2, 1997, Pat. No. 5,852,022, which is a continuation of application No. 08/470,400, Jun. 6, 1995, abandoned.

[51] Int. Cl.$^6$ ............... A61K 31/55; A61K 31/495; C07D 243/08; C07D 413/00
[52] U.S. Cl. ............... 514/218; 514/255; 544/368; 540/575
[58] Field of Search ............... 540/575; 544/368; 514/218, 255

[56] References Cited

U.S. PATENT DOCUMENTS

| | | | |
|---|---|---|---|
| 4,411,901 | 10/1983 | Temple, Jr. et al. | 424/250 |
| 4,806,649 | 2/1989 | Strupczewski | 546/193 |
| 4,853,470 | 8/1989 | Strupczewski | 546/199 |
| 4,954,503 | 9/1990 | Strupczewski et al. | 514/441 |
| 5,077,405 | 12/1991 | Strupczewski | 544/366 |
| 5,206,366 | 4/1993 | Bowles et al. | 544/368 |
| 5,494,908 | 2/1996 | O'Malley et al. | 514/228.2 |

FOREIGN PATENT DOCUMENTS

| | | |
|---|---|---|
| 0 279 598 | 8/1988 | European Pat. Off. . |
| 0 302 423 | 2/1990 | European Pat. Off. . |
| 0 398 425 | 11/1990 | European Pat. Off. . |
| 0 402 644 | 12/1990 | European Pat. Off. . |
| 0 494 817 | 7/1992 | European Pat. Off. . |
| 32 47 530 | 6/1983 | Germany . |
| 2 163 432 | 2/1980 | United Kingdom . |
| WO 92/17475 | 10/1992 | WIPO . |
| WO 93/09102 | 5/1993 | WIPO . |
| WO 94/12495 | 6/1994 | WIPO . |

*Primary Examiner*—Mukund J. Shah
*Assistant Examiner*—Bruck Kifle
*Attorney, Agent, or Firm*—Frommer Lawrence & Haug LLP

[57] ABSTRACT

This invention relates to compounds of the formula

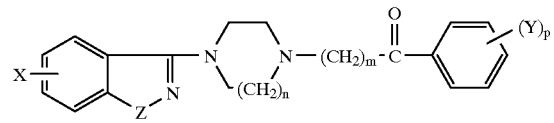

wherein X, Y, Z, m, n and p are as defined within, pharmaceutical compositions containing these compounds and to their use as antipsychotic agents, particularly in the treatment of schizophrenia. Depot derivatives of the compounds are useful for providing long acting effects of the compounds.

10 Claims, No Drawings

ANTIPSYCHOTIC AGENTS, COMPOSITIONS AND METHOD OF USE

This application is a division of application Ser. No. 08/921,480 filed Sep. 2, 1997, now U.S. Pat. No. 5,852,022, which is a continuation of application Ser. No. 08/470,400 filed Jun. 6, 1995, now abandoned.

This invention relates to heteroarylpiperazines having antipsychotic activity and to their use as antipsychotic drugs.

The therapeutic treatment of schizophrenic patients by administration of neuroleptic drugs, such as chlorpromazine, haloperidol, sulpiride, and chemically closely related compounds, is widespread. While control of schizophrenic symptoms has been successful, treatment with these drugs does not cure the psychotic patient, who will almost certainly relapse if medication is discontinued. There exists a continuing need in the art for antipsychotic drugs for the treatment of psychoses.

Moreover, some of the known neuroleptics produce unwanted side effects. For example, the side effects of many antipsychotic drugs include the so-called extrapyramidal symptoms, such as rigidity and tremor, continuous restless walking, and tardive dyskinesia which causes facial grimacing, and involuntary movements of the face and extremities. Orthostatic hypotension is also common. Thus, there also exists a need in the art for antipsychotic drugs that produce fewer or less severe manifestations of these common side effects.

In addition, because of the frequent long term administration of neuroleptics and the problems with patient compliance, there is a further need in the art for long lasting neuroleptics, which can be formulated into sustained release depot preparations, without the side effects previously mentioned.

This invention relates to a compound of the formula

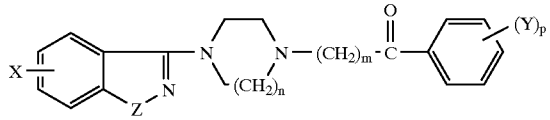

wherein

X is —OH, —OC(=O)($C_1$–$C_{18}$)alkyl, —OC(=O)($C_6$–$C_{10}$)aryl, —OC(=O)($C_1$–$C_{12}$)alkyl($C_6$–$C_{10}$)aryl, —OC(=O)NH($C_1$–$C_{18}$)alkyl, —OC(=O)($C_1$–$C_{12}$)alkyl($C_3$–$C_8$)cycloalkyl, —OC(=O)O($C_1$–$C_{18}$)alkyl, or —OC(=O)—($C_3$–$C_{12}$)cycloalkyl;

Y is hydrogen, halogen, trifluoromethyl, ($C_1$–$C_6$)alkoxy, cyano or nitro;

Z is O or $NR_1$;

$R_1$ is hydrogen, ($C_1$–$C_6$)alkyl, formyl, —C(=O)($C_1$–$C_{18}$)alkyl, or —C(=O)O($C_1$–$C_{18}$)alkyl;

m is 1, 2, 3 or 4;

n is 1 or 2; and p is 1 or 2; and its pharmaceutically acceptable acid addition salts; pharmaceutical compositions containing these compounds and their use as antipsychotic agents, particularly in the treatment of schizophrenia. The compounds of the invention are atypical antipsychotic agents.

This invention also provides compounds which are suitable for acylation with ($C_1$–$C_{18}$)carboxylic acids or reactive functional derivatives thereof to form highly lipophilic esters, amides and carbamates, which compounds are also compounds of this invention. Such selected compounds possess a hydroxyl group attached to either an aromatic carbon atom capable of forming the highly lipophilic esters of the invention or a secondary nitrogen atom including the nitrogen at the 1-position of an indazole ring system capable of forming the highly lipophilic amides of the invention. The secondary nitrogen atom may alternatively be acylated with a ($C_1$–$C_{18}$)alkoxy-carbonyl chloride to form a highly lipophilic carbamate derivative of the invention.

The invention also provides for the highly lipophilic compounds which provide long acting pharmaceutical effects when administered in the form of depot preparations.

This invention also provides a pharmaceutical composition, which comprises a compound of the invention and a pharmaceutically acceptable carrier therefor. In one embodiment of the invention, the pharmaceutical composition is an antipsychotic composition comprising a compound of the invention in an amount sufficient to produce an antipsychotic effect.

In addition, this invention provides a method of treating psychoses, which comprises administering to a patient a pharmaceutically effective amount of a compound of the invention.

Further, this invention provides a method of sustained release of a pharmaceutically effective amount of a lipophilic compound of the invention in the form of a depot preparation.

Unless otherwise stated or indicated, the following definitions shall apply throughout the specification and the appended claims.

The term ($C_1$–$C_{18}$)alkyl shall mean a straight or branched alkyl group, for example, methyl, ethyl, n-propyl, isopropyl, tert-butyl, n-butyl, isobutyl, sec-butyl and straight and branched chain pentyl, hexyl, heptyl, decyl, undecyl, dodecyl, etc. up to an 18 carbon chain length.

The term halo or halogen shall mean fluorine, chlorine, bromine or iodine.

The term ($C_3$–$C_{12}$)cycloalkyl shall mean monocyclo and polycyclo alkyl rings such as cyclopropyl, cyclobutyl, cyclopentyl, cyclohexyl, cycloheptyl, adamantyl, norbornyl and the like.

The term ($C_6$–$C_{10}$)aryl shall mean aromatic carbocyclic rings such as benzene and naphthalene.

Throughout the specification and the appended claims, a given formula or name shall encompass all stereo, optical, enantiomeric and tautomeric isomers where such isomers exists.

In one class of compounds of this invention is a compound of the formula

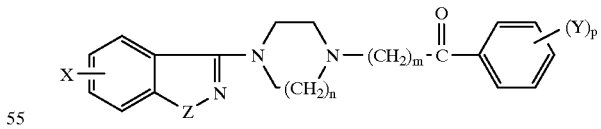

wherein

X is —OH, —OC(=O)($C_1$–$C_{18}$)alkyl, —OC(=O)NH($C_1$–$C_{18}$)alkyl, —OC(=O)O($C_1$–$C_{18}$)alkyl or —OC(=O)—($C_3$–$C_{12}$)cycloalkyl;

Y is hydrogen, halogen, trifluoromethyl, ($C_1$–$C_6$)alkoxy, cyano or nitro;

Z is O or $NR_1$;

$R_1$ is hydrogen, ($C_1$–$C_6$)alkyl, formyl, —C(=O)($C_1$–$C_{18}$)alkyl or —C(=O)O($C_1$–$C_{18}$)alkyl;

m is 1, 2, 3 or 4;

n is 1 or 2; and p is 1 or 2; and its pharmaceutically acceptable acid addition salts.

In a preferred embodiment of this class is a compound of the formula

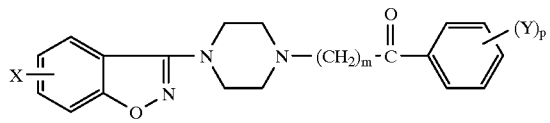

wherein

X is —OH, —OC(=O)(C$_1$-C$_{18}$)alkyl, —OC(=O)NH(C$_1$-C$_{18}$)alyl, —OC(=O)O(C$_1$-C$_{18}$)alkyl or —OC(=O)—(C$_3$-C$_{12}$)cycloalkyl;

Y is hydrogen or halogen;

m is 1, 2, 3 or 4; and p is 1; and its pharmaceutically acceptable acid addition salts.

More preferably, m is 3 and Y is 4-fluoro.

Most preferably X is 6-hydroxy, 6—OC(=O)NHbutyl, 6—OC(=O)Ohexyl, 6—OC(=O)nonyl, or 6—OC(=O)adamantyl; and its pharmaceutically acceptable acid addition salts.

In another preferred embodiment of this class is a compound of the formula

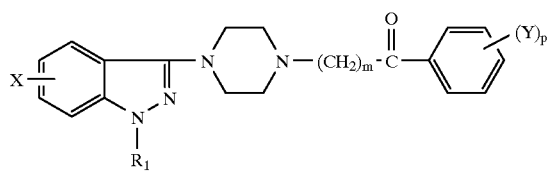

wherein

X is —OH, —OC(=O)(C$_1$-C$_{18}$)alkyl, —OC(=O)NH(C$_1$-C$_{18}$)alkyl, —OC(=O)O(C$_1$-C$_{18}$)alkyl or —OC(=O)—(C$_3$-C$_{12}$)cycloalkyl;

Y is hydrogen or halogen;

R$_1$ is hydrogen, (C$_1$-C$_6$)alkyl, formyl, —C(=O)(C$_1$-C$_{18}$)alkyl, or —C(=O)O (C$_1$-C$_{18}$)alkyl;

m is 1, 2, 3 or 4; and p is 1; and its pharmaceutically acceptable acid addition salts.

More preferably, m is 3 and Y is 4-fluoro.

Most preferably, X is 6-hydroxy, 6—OC(=O)NHbutyl, 6—OC(=O)Ohexyl, 6—OC(=O)nonyl, or 6—OC(=O)adamantyl; and R$_1$ is hydrogen or —C(=O)nonyl; and its pharmaceutically acceptable acid addition salts.

In another class of compounds of this invention is a compound of the formula

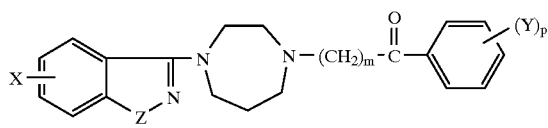

wherein

X is —OH, —OC(=O)(C$_1$-C$_{18}$)alkyl, —OC(=O)NH(C$_1$-C$_{18}$)alkyl, —OC(=O)O(C$_1$-C$_{18}$)alkyl or —OC(=O)—(C$_3$-C$_{12}$)cycloalkyl;

Y is hydrogen, halogen, trifluoromethyl, (C$_1$-C$_6$)alkoxy, cyano or nitro;

Z is O or NR$_1$;

R$_1$ is hydrogen, formyl, (C$_1$-C$_6$)alkyl, —C(=O)(C$_1$-C$_{18}$)alkyl, or —C(=O)O(C$_1$-C$_{18}$)alkyl;

m is 1, 2, 3 or 4; and p is 1 or 2; and its pharmaceutically acceptable addition salts.

In a preferred embodiment of this class is a compound of the formula

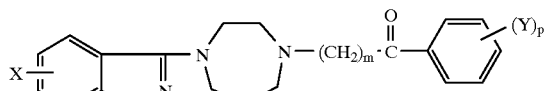

wherein

X is —OH, —OC(=O)(C$_2$-C$_{18}$)alkyl, —OC(=O)NH(C$_1$-C$_{18}$)alkyl, —OC(=O)O(C$_1$-C$_{18}$)allyl or —OC(=O)—(C$_3$-C$_{12}$)cycloalkyl;

Y is hydrogen or halogen;

m is 1, 2, 3 or 4; and p is 1; and its pharmaceutically acceptable acid addition salts.

More preferably, m is 3 and Y is 4-fluoro.

Most preferably, X is 6-hydroxy, 6—OC(=O)NHbutyl, 6—OC(=O)Ohexyl, 6—OC(=O)nonyl, or 6—OC(=O)adamantyl; and its pharmaceutically acceptable acid addition salts.

In another preferred embodiment of this class are compounds of the formula

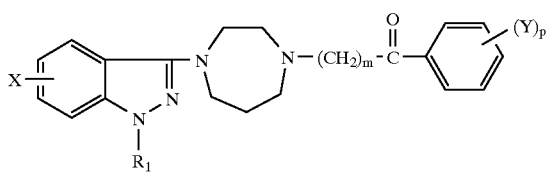

wherein

X is —OH, —OC(=O)(C$_1$-C$_{18}$)alkyl, —OC(=O)NH(C$_1$-C$_{18}$)alkyl, —OC(=O)O(C$_1$-C$_{18}$)alkyl or —OC(=O)—(C$_3$-C$_{12}$)cycloalkyl;

Y is hydrogen or halogen;

R$_1$ is hydrogen, (C$_1$-C$_6$)alkyl, formyl, —C(=O)(C$_1$-C$_{18}$)alkyl, or —C(=O)O(C$_1$-C$_{18}$)alkyl;

m is 1, 2, 3 or 4;

n is 1; and p is 1 or 2; and its pharmaceutically acceptable acid addition salts.

More preferably, m is 3 and Y is 4-fluoro.

Most preferably, X is 6-hydroxy, 6—OC(=O)NHbutyl, 6—OC(=O)Ohexyl, 6—OC(=O)nonyl, or 6—OC(=O)adamantyl; and R$_1$ is hydrogen or —C(=O)nonyl; and its pharmaceutically acceptable acid addition salts.

Nonlimiting examples of compounds of the invention include:

3-[1-(4'-Fluorobenzoyl)propyl4-piperazinyl]-6-hydroxy-1,2-benzisoxazole

3-[1-(4'-Fluorobenzoyl)propyl-4-piperazinyl]-5-hydroxy-1,2-benzisoxazole

3-[1-(4'-Fluorobenzoyl)propyl-4-piperazinyl]-4-hydroxy-1,2-benzisoxazole

3-[1-(4'-Fluorobenzoyl)propyl-4-piperazinyl]-7-hydroxy-1,2-benzisoxazole
3-[1-(4'-Fluorobenzoyl)propyl-4-piperazinyl]-6-hydroxy-1,2-benzisoxazole hydrobromide
3-[1-(4'-Fluorobenzoyl)propyl-4-piperazinyl]-6-hydroxy-1,2-benzisoxazole hydrochloride
3-[1-(4'-Fluorobenzoyl)butyl-4-piperazinyl]-6-hydroxy-1,2-benzisoxazole
3-[1-(4'-Fluorobenzoyl)ethyl-4-piperazinyl]-6-hydroxy-1,2-benzisoxazole
3-[1-(4'-Fluorobenzoyl)methyl-4-piperazinyl]-6-hydroxy-1,2-benzisoxazole
Butyl carbamic acid 3-[4-[4-(4-fluorophenyl)4-oxo-butyl]-piperazin-1-yl]-1,2-benzisoxazol-6-yl ester
Hexyl carbamic acid 3-[4-[4-(4-fluorophenyl)-4-oxo-butyl]-piperazin-1-yl]-1,2-benzisoxazol-6-yl ester
Dodecyl carbamic acid 3-[4-[4-(4-fluorophenyl)-4-oxo-butyl]-piperazin-1-yl]-1,2-benzisoxazol-6-yl ester
Octadecyl carbamic acid 3-[4-[4-(4-fluorophenyl)4-oxo-butyl]-piperazin-1-yl]-1,2-benzisoxazol-6-yl ester
Decanoic acid 3-[4-[4-(4-fluorophenyl)-4-oxo-butyl]-piperazin-1-yl]-1,2-benzisoxazol-6-yl ester
Dodecanoic acid 3-[4-[4-(4-fluorophenyl)4-oxo-butyl]-piperazin-1-yl]-1,2-benzisoxazol-6-yl ester
Hexadecanoic acid 3-[4-[4-(4-fluorophenyl)4-oxo-butyl]-piperazin-1-yl]-1,2-benzisoxazol-6-yl ester
Octadecanoic acid 3-[4-[4-(4-fluorophenyl)4-oxo-butyl]-piperazin-1-yl]-1,2-benzisoxazol-6-yl ester
Adamantane-1-carboxylic acid $^3$-[$^4$-[$^4$-(4-fluorophenyl)4-oxo-butyl]-piperazin-1-yl]-1,2-benzisoxazol-6-yl ester
Cyclohexylhexanoic acid 3-[4-[4-(4-fluorophenyl)4-oxo-butyl]-piperazin-1-yl]-1,2-benzisoxazol-6-yl ester
Cyclohexylcarboxylic acid 3-[4-[4-(4-fluorophenyl)-4-oxo-butyl]-piperazin-1-yl]-1,2-benzisoxazol-6-yl ester
Carbonic acid (3-[4-[4-(4-fluorophenyl)4-oxo-butyl] piperazin-1-yl]-1,2-benzisoxazol-6-yl)ester hexyl ester
Carbonic acid (3-[4-[4-(4-fluorophenyl)-4-oxo-butyl] piperazin-1-yl]-1,2-benzisoxazol-6-yl)ester dodecyl ester
Carbonic acid (3-[4-[4-(4-fluorophenyl)-4-oxo-butyl] piperazin-1-yl]-1,2-benzisoxazol-6-yl)ester octadecyl ester
3-[1-(4'-Fluorobenzoyl)propyl-4-homopiperazinyl]-6-hydroxy-1,2-benzisoxazole
Butyl carbamic acid 3-[4-[4-(4-fluorophenyl)-4-oxo-butyl]-homopiperazin-1-yl]-1,2-benzisoxazol-6-yl ester
Decanoic acid 3-[4-[4-(4-fluorophenyl)-4-oxo-butyl]-homopiperazin-1-yl]-1,2-benzisoxazol-6-yl ester
Carbonic acid (3-[4-[4-(4-fluorophenyl)-4-oxo-butyl] homopiperazin-1-yl]-1,2-benzisoxazol-6-yl)ester hexyl ester
3-[1-(4'-Fluorobenzoyl)propyl-piperazinyl]-6-hydroxy-1H-indazole
3-[1-(4'-Fluorobenzoyl)propyl-4-piperazinyl]-6-hydroxy-1H-indazole hydrochloride
Butyl carbamic acid 3-[4-[4-(4-fluorophenyl)-4-oxo-butyl]-piperazin-1-yl]-1H-indazol-6-yl ester
Octadecanoic acid 3-[4-[4-(4-fluorophenyl)-4-oxo-butyl]-piperazin-1-yl]-1H-indazol-6-yl ester
Carbonic acid (3-[4-[4-(4-fluorophenyl)4-oxo-butyl]-piperazin-1-yl]-1H-indazol-6-yl)ester octadecyl ester The compounds of the invention can be synthesized using one or more of the following general procedures described below.

Throughout the description of the synthetic procedures, the notations X, Y, m, n and p have the respective meanings given above unless otherwise stated or indicated, R is $(C_1-C_{18})$alkyl, $(C_6-C_{10})$aryl, $(C_1-C_{12})$alkylaryl, $(C_1-C_{12})$alyky$(C_3-C_8)$cycloalkyl or $(C_3-C_{12})$cycloalkyl, and other notations have the respective meanings defined in their first appearances.

More particularly, as shown in Reaction Scheme A, the benzoxazoles are prepared from the chloro compound of Formula III, where X is alkoxy, is reacted with the cyclic amine of the formula IV to form the compound of Formula V where X is alkoxy.

The reaction is typically carried out neat in a sealed tube or under nitrogen at a temperature of from about 100° C. to about 200° C., preferably from about 120° C. to about 180° C., most preferably from about 130° C. to about 150° C. for from about 0.5 hour to about 100 hours, preferably from about 0.5 hours to about 8 hours, most preferably from about 0.45 hours to about 6 hours.

The compound of Formula V is then reacted with the haloalkylphenone compound of Formula VI to provide the compound of Formula VII wherein X is alkoxy. The reaction can be carried out in a polar non-protic organic solvent such as, for example, acetonitrile, at a temperature of from about 0° C. to about 120° C., preferably from about 60° C. to about 100° C., most preferably at about 80° C. for from about 0.5 hours to about 24 hours, preferably for from about 1 hour to about 12 hours, most preferably for about 4 to 6 hours. The reaction is generally carried out in the presence of a base such as potassium or sodium carbonate and a catalyst such as potassium iodide.

The indazoles are prepared as shown in Reaction Scheme B, starting from the appropriate acetophenone of Formula IX wherein X is alkoxy which is oxidized to the corresponding carboxylic acid of Formula X wherein X is alkoxy under known conditions such as in the presence of sodium hydroxide and bromine.

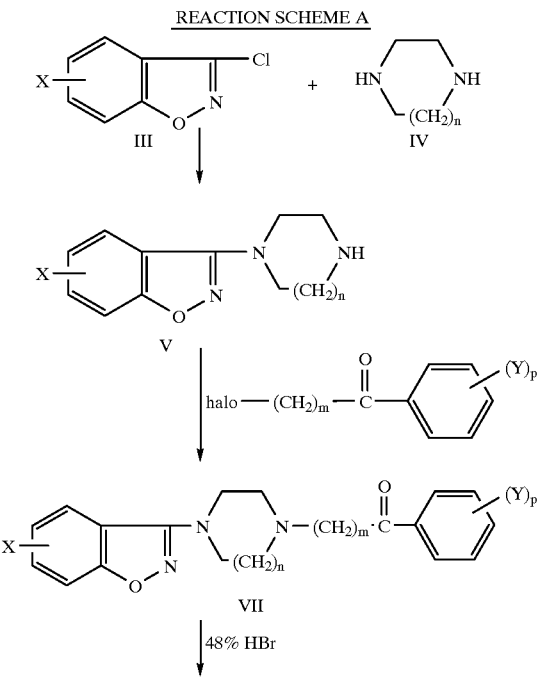

REACTION SCHEME A

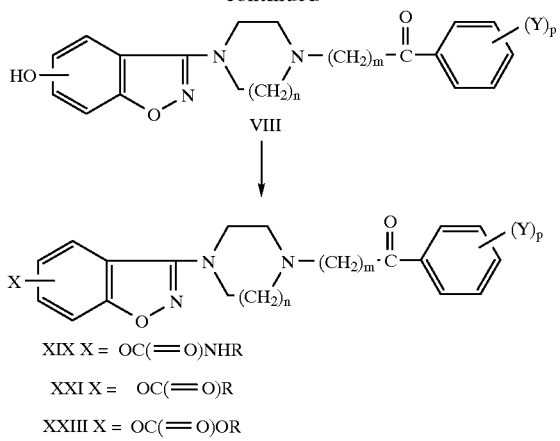

The acid of Formula X wherein X is alkoxy is then treated with sulfonyl chloride and p-toluenesulfonhydrazide under known conditions to form the hydrazide of Formula XI which is further treated with sulfonyl chloride under known conditions to yield the chlorotosylhydrazone of Formula XII wherein X is alkoxy.

The chlorotosylhydrazone of Formula XII wherein X is alkoxy is reacted with the appropriate phenylpiperazinyl ketone of Formula XIII (prepared from the appropriate haloalkylphenone and piperazine under known conditions) to yield the hydrazono compound of Formula XIV wherein X is alkoxy. The reaction is typically carried out in an organic solvent at from about 0° C. to about 50° C., preferably from about 10° C. to about 35° C., most preferably at about room temperature.

The compound of Formula XIV is then heated in a polar non-protic solvent such as dimethylformamide for from about 1 hour to about 24 hours, more preferably from about 2 hours to about 12 hours, most preferably from about 3 hours to about 6 hours at a temperature of from about 35° C. to about 125° C., more preferably from about 50° C. to about 100° C., most preferably at about 90° C. to yield the compound of Formula XV.

The compound of Formula XV is heated in the presence of hydrochloric acid to form the compound of Formula XVI wherein X is alkoxy.

The compound of Formula XVI is alkylated under known conditions, such as with dimethylsulfate in the presence of a base such as potassium carbonate in a non-protic organic solvent to form the compound of Formula XVII.

The compounds of Formula VII and XVII when X is alkoxy can be treated with acid such as, for example, 48% hydrobromic acid to yield the corresponding hydroxy compounds of Formula VIII and XVIII. The reaction is typically carried out at reflux for from about 1 hour to about 12 hours, preferably from about 2 hours to about 4 hours.

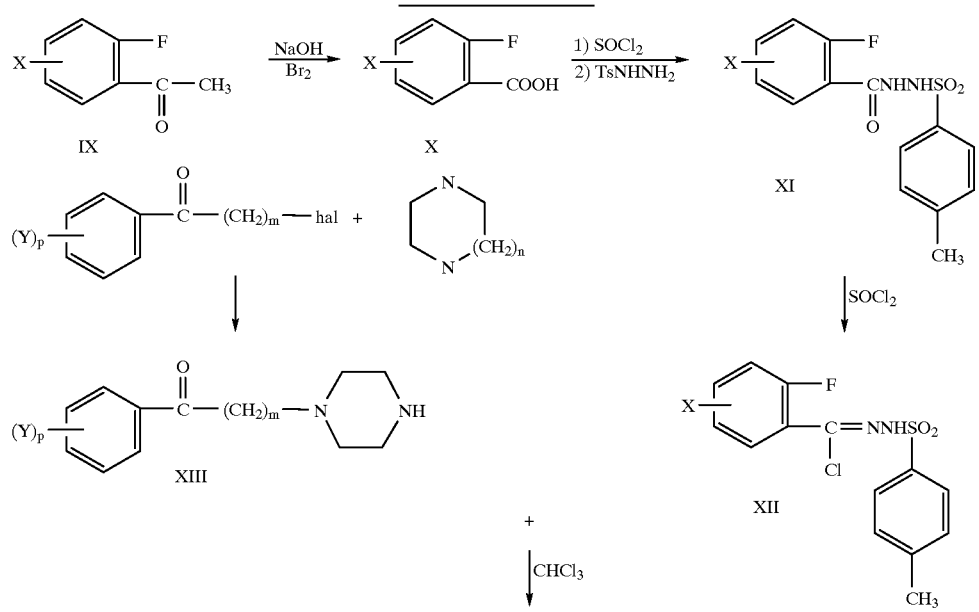

-continued

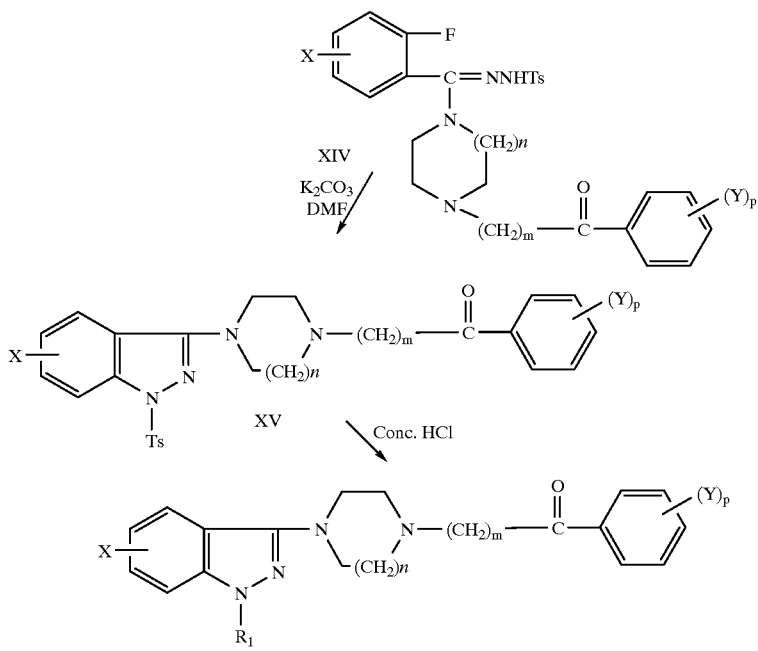

XVI  X = OR, R₁ = H
XVII X = OR, R₁ = alkyl
XVIII X = OH, R₁ = alkyl
XX   X = OC(═O)NHR, R₁ = alkyl
XXII X =OC(═O)R, R₁ = alkyl
XXIV X =OC(═O)OR, R₁ = alkyl The hydroxy compounds of Formula VIII and XVIII are treated with the appropriate isocyanate, carbamoylchloride or carbonyldimidazole and an amine to obtain the corresponding compounds of Formula XIX and XX where R is ($C_1$–$C_{18}$)alkyl or aryl($C_1$–$C_{10}$)alkyl. The reaction is carried out in an inert organic solvent such as, for example, ethyl acetate for from about 0.5 hours to about 24 hours, optionally in the presence of a catalyst such as, for example, copper(I)chloride.

Additionally, the hydroxy compounds of Formula VIII and XVIII are treated with an alkyl, aryl or aralkylcarboxylic acid halide, such as for example, adamantanecarbonyl chloride or decanoyl chloride, under basic conditions known in the art to yield the corresponding alkoxy, aryloxy or aralkyloxy compounds of Formula XXI and XXII.

The hydroxy compounds of Formula VIII and XVIII are also reacted under basic conditions known in the art with the appropriate chloroformate to yield the carbonate compounds of Formula XXIII and XXIV.

In the case of the indazoles, the nitrogen at the 1-position of the indazole can also be substituted by means known in the art.

The preparation of the starting materials is known in the art. For example, the preparation of the compounds of Formula III is disclosed in WO 9412495A1.

Selected compounds of the invention possess a hydroxyl or amine group attached to either an aliphatic or aromatic carbon capable of forming the highly lipophilic esters or amides of this invention The hydroxy group may alternatively be acylated with a ($C_1$–$C_{18}$) alkoxycarbonyl chloride to form a highly lipophilic carbonate derivative or with a ($C_1$–$C_{18}$) carbamoylhalide to form a highly lipophilic carbamate derivative. Representatives of such alcohols and amines and their highly lipophilic derivatives are found in the Examples of this invention.

It is known in the art that long acting derivatives of drugs may be obtained by such transformation. European Patent Publication No. 260,070 discloses the prolonged action of haloperidol decanoate ester. International Publication No. WO 92/06089 discloses sustained release amide derivatives of sertindole.

The compounds of the present invention are useful for treating psychoses by virtue of their ability to elicit an antipsychotic response in mammals. In particular, the present compounds are potent atypical antipsychotic agents, i.e. compounds which display a $D_2$/5-$HT_2$ affinity ratio of greater than 1. The compounds of the invention further show a reduced potential for extra pyramidal side effects (EPS) as evidenced by a large difference in $ED_{50}$ for the Climbing Mouse Assay (CMA) and the Apomorphine Induced Stereotypy in Rats Test (APO-S).

It is known that it is possible to predict antipsychotic efficacy and potential side effect liability by observing the electrophysiological profile of a drug on the dopamine (DA) neurons in the mesolimbic (A10) and nigrostriatal (A9) regions, respectively, of the rat brain. Thus, it has been shown by utilizing extracellular single unit recording techniques that all compounds that were effective antipsychotics both classic and atypical, would cause, upon repeated administration, a tonic depolarization inactivation of the A10 DA neurons. Such a result would support the hypothesis that the symptoms of schizophrenia are predominantly due to excess DA activity in the mesolimbic area of the brain. However, it has also been shown that classic antipsychotics, those known to have EPS liability, such as haloperidol, would additionally cause a depolarization inactivation of the DA neurons in the A9 area of the brain. As this area of the brain has been linked to motor function, the inhibition of these neurons provided a rationale for the EPS liability of the typical antipsychotics. The compounds of the invention show a significant decrease in the number of spontaneously active DA neurons in the A10 area of the brain. However, similar to clozapine and unlike haloperidol, the compounds of the invention do not cause a decrease in the number of DA neurons in the A9 area. This result strongly suggests that the compounds should be affective antipsychotics with little propensity to cause EPS.

CLIMBING MOUSE ASSAY

Antipsychotic activity is determined in the climbing mice assay by a method similar to those described by P. Protais, et al., Psychopharmacol., 50:1 (1976) and B. Costall, Eur. J. Pharmacol., 50:39 (1978).

Subject CK-1 male mice (23–27 grams) are group-housed under standard laboratory conditions. The mice are individually placed in wire mesh stick cages (4"×10") and are allowed one hour for adaption and exploration of the new environment. Then apomorphine is injected subcutaneously at 1.5 mg/kg, a dose causing climbing in all subjects for 30 minutes. Compounds to be tested for antipsychotic activity are injected intraperitoneally or given oral doses at various time intervals, e.g. 30 minutes, 60 minutes, etc. prior to the apomorphine challenge at a screening dose of 10–60 mg/kg.

For evaluation of climbing, 3 readings are taken at 10, 20, and 30 minutes after apomorphine administration according to the following scale:

| Climbing Behavior Mice With: | Score |
| --- | --- |
| 4 paws on bottom (no climbing) | 0 |
| 2 paws on the wall (rearing) | 1 |
| 4 paws on the wall (full climb) | 2 |

Mice consistently climbing before the injection of apomorphine are discarded.

With full-developed apomorphine climbing, the animals are hanging on to the cage walls, rather motionless, over long periods of time. By contrast, climbs due to mere motor stimulation usually only last a few seconds.

The climbing scores are individually totaled (maximal score: 6 per mouse over 3 readings) and the total score of the control group (vehicle intraperitioneally, apomorphine subcutaneously) is set to 100%. $ED_{50}$ values with 95% confidence limits, calculated by a linear regression analysis, of some of the compounds of the present invention as well as reference standard antipsychotic agents are presented in Table 1.

TABLE 1

| COMPOUND | CLIMBING MOUSE ASSAY ($ED_{50}$ mg/kg, ip) |
| --- | --- |
| 3-[1-(4'-Fluorobenzoyl)propyl-4-piperazine]-6-methoxy-1,2-benzisoxazole | 5.28 |
| 3-[1-(4'-Fluorobenzoyl)propyl-4-piperazinyl]-6-hydroxy-1,2-benzisoxazole hydrobromide | 0.4 |
| Clozapine (reference) | 8.1 |
| Haloperidol (reference) | 0.11 |

APOMORPHINE STEREOTYPY INHIBITION IN RATS

Purpose

To screen neurolepic compounds which act directly on the dopaminergic system by blocking the action of apomorphine on postsynaptic dopamine receptors (Anden et al., 1967; Ernst, 1967).

Method

The subjects are male Wistar rats (125–250 grams) housed under standard laboratory conditions. For a primary screen, a group size of six is used. Drug is administered one hour prior to scoring and the animals are placed in individual clear plastic cages (24×14×13 cm). The control group receives vehicle. Apomorphine is prepared at a concentration of 15 mg/10 ml in a 0.003% ascorbic acid stock solution prepared with 30 mg of ascorbic acid in 100 ml of 1% saline to increase the stability of the apomorphine while in solution. Apomorphine is admininistered at a dose of 1.5 mg/kg subcutaneously (s.c.) with a dosage volume of 1 ml/kg 50 minutes after test compound or vehicle administration. Stereotypic behavior is noted 10 minutes later. Stereotypy occurs in a repetitive manner and is continuous for a 10 second period in the presence of white noise. Stereotypic behavior is defined as sniffing, licking or chewing behavior which occurs in a repetitive manner and is continuous for a 10-second period in the presence of white noise. The animal is considered protected if this behavior is interrupted. The percent effectiveness of a drug is determined by the number of animals protected in each group.

A dose-response is determined in the same manner as a primary screen except that a group size of 10 is used and the animals are dosed in a randomized manner. One group receives vehicle. $ED_{50}$ values for inhibition of stereotypy are calculated by means of Litchfield and Wilcoxon Analysis.

Compounds preventing the stereotypy behavioral response to apomorphine are verified to have postsynaptic dopamine receptor antagonist properties.

References

Anden, N. E., Rubenson, A., Fuxe, K. and Kokfelt, T. evidence for dopamine receptor stimulation by apomorphine. J. Pharm. Pharmacol, 19: 627–629, 1967.

Ernst, A. M. Mode of action of apomorphine and dexamphetamine on gnawing compulsion in rats. Psychopharmacologia (Berl.,) 10:316–323, 1967.

The $ED_{50}$ values are set forth in Table 2.

TABLE 2

| COMPOUND | APOMORPHINE STEREOTYPY INHIBITION ($ED_{50}$ mg/kg, ip or % inhibition) |
| --- | --- |
| 3-[1-(4'-Fluorobenzoyl)propyl-4-piperazinyl]-6-hydroxy-1,2-benzoisoxazole hydrobromide | 0% at 4.0 mg/kg. |
| Clozapine | >40 mg/kg. |
| Haloperidol | $ED_{50}$ = 0.6 mg/kg, ip. |

$D_2$/5-$HT_2$ BINDING ASSAYS

$^3$H-Spiroperidol Binding to Striatal Membranes ($D_2$-Dopaminergic Site) in Rats Assays were run according to the method of Leysen et al. [1978]. Striatal membranes were incubated with $^3$H-spiroperidol (0.4 nM) and various concentrations of test drug at 37 C. for 10 minutes in 1 ml of 0.05 M Tris-HCl buffer, pH 7.7 containing 120 mM NaCl, 5 mM KCl, 2mM $CaCl_2$, and 1 mM $MgCl_2$. Nonspecific binding was determined in the presence of $2\mu M(+)$-butaclamol. Bound ligand was separated by rapid filtration through Whatman GF/B filters.

$^3$H-Spiroperidol Binding to Cerebral Cortical membranes (5$HT_2$ Site) in Rats Assays were performed by a modification of the method of Peroutka and Snyder [1979]. Cortical membranes were incubated with $^3$H-spiroperidol (1.5 nM) and various concentrations of test drug at 37° C. for 10 minutes in 1 ml of 0.05 M Tris-HCl buffer, pH 7.7 containing 120 mM NaCl, 5 mM KCl, 2 mM CaCl$_2$, and 1 mM MgCl$_2$. Nonspecific binding was determined in the presence of 5 μM methysergide. The incubation was terminated by rapid filtration through Whatman GF/B filters.

The results are set forth in Table 3.

TABLE 3

| COMPOUND | D$_2$ IC$_{50}$ | 5-HT$_2$ IC$_{50}$ | D$_2$/5-HT$_2$ |
|---|---|---|---|
| 3-[1-(4'-Fluorobenzoyl)-propyl-4-piperazinyl]-6-hydroxy-1,2-benzisoxazole hydrobromide | 0.24 μM | 0.045 μM | 5.3 |
| Clozapine | 0.83 μM | 0.05 μM | 17 |
| Haloperidol | 0.018 μM | 0.17 μM | 0.1 |

DOPAMINE NEURON SAMPLING

Dopamine Neuron Sampling. Male Wistar rats (280–360 grams) were used in this procedure. They were housed for at least 48 hours in a climate-controlled vivarium with food and water continuously available. Each rat was initially anesthetized with chloral hydrate (400 mg/kg ip) and maintained with additional injections as needed throughout the experiment. The animal was mounted in a stereotaxic apparatus (Kopf, model 900). The cranium was exposed., cleaned of connective tissue and dried. The skull overlying both the substantia nigra [A9:anterior (A) 3000–3400 microns, lateral (L) 1800–2400 microns from lambda)] and the ventral tegmental area (Al 0: A 3000–3400 microns, L 400–1000 microns from lambda)[47] was removed. Using the dura as a point of reference, a micropipette driven by a hydraulic microdrive was lowered through the opening in the skull at vertical 6000–8500 microns. Spontaneously firing dopamine neurons within both the substantia nigra and the ventral tegmental areas were counted by lowering the electrode into twelve separate tracks (each track separated from the other by 200 microns) in each region. The sequence of the tracks was kept constant, forming a block of tissue which could be reproducibly located from animal to animal.

Extracellular neuronal signals were sampled using a single barrel micropipette approximately one micron at its tip, and filled with 2 M NaCl saturated with 1% pontamine sky blue dye. The in vitro impedance of this pipet (measured with a Winston Electronics Co., BL-1000 Micro Electrode Tester) was between 5 and 10 megaohms. Electrical potentials were passed through a high-impedance preamplifier and the signal was sent to a window discriminator (WPI model 121) which converted potentials above background noise levels to discrete pulses of fixed amplitude and duration. Only cells whose electrophysiological characteristics matched those previously established for midbrain dopamine neurons were counted. In an anesthetized rat, a neuron was considered to be dopaminergic if it displayed a triphasic postive-negative-postive spike profile of 0.4 to 1.5 microvolts amplitude and 2.5 milliseconds duration, firing in an irregular pattern of 3 to 9 Hz with occasional bursts characterized by progressively decreasing spike amplitude and increasing spike duration.

At the end of each experiment, the location of the last recorded track tip was marked by passing 25 microampere cathodal current through the recording micropipette barrel for 15 minutes in order to deposit a spot of dye. The rat was sacrificed; the brain was then removed, dissected and frozen on a bed of dry ice. Frozen serial sections (20 microns in width) were cut, mounted, and stained with cresyl violet and examined using a light microscope.

Animals pretreated with vehicle prior to neuronal sampling served as controls. Compounds were prepared as percent base. Each compound was suspended in distilled water and one drop of Tween 80, and kept constantly agitated during dosing. All compounds were delivered at a dosage volume of 1 mg/kg by the intraperitoneal route. For animals used in the chronic single-unit, dopamine neuron sampling assay, the compounds were administered once a day for 21 days, and dopamine neuron sampling was begun two hours after the last dose on the 21st day. Drug treatment groups were compared to vehicle groups with a one-way ANOVA with a post hoc Neuman-Keuls analysis for significance.

The results are set forth in Table 4.

TABLE 4

CHRONIC SINGLE DOPAMINE NEURON SAMPLING IN RATS

| Compound | % Change in A10 region | % Change in A9 region |
|---|---|---|
| 3-[1-(4'-Fluorobenzoyl)-propyl-4-piperazinyl]-6-hydroxy-1,2-benzisoxazole hydrobromide at 20 mg/kg, ip. | −44.9 | +14 |
| Clozapine (atypical reference drug) | −79 | +37 |
| Haloperidol (atypical reference drug) | −35 | −30 |

Antipsychotic response is achieved when compounds of the present invention are administered to a subject requiring such treatment as an effective oral, parenteral, or intravenous dose of from 0.01 to 50 mg/kg of body weight per day. It is to be understood, however, that for any particular subject, specific dosage regimens should be adjusted according to the individual need and the professional judgment of the person administering or supervising the administration of the aforesaid compound. It is to be further under stood that the dosages set forth herein are exemplary only and they do not, to any extent, limit the scope or practice of the invention.

Effective amounts of the compounds of the present invention can be administered to a subject by any one of several methods, for example, orally as in capsules or tablets, parenterally in the form of sterile solutions or suspensions, and in some cases intravenously in the form of sterile solutions.

The compounds of the present invention, while effective themselves, can be formulated and administered in the form of their pharmaceutically acceptable addition salts for purposes of stability, convenience of crystallization, increased solubility, and the like. Preferred pharmaceutically acceptable addition salts include salts of mineral acids, for example, hydrochloric acid, sulfuric acid, nitric acid, and the like; salts of monobasic carboxylic acids, for example, acetic acid, propionic acid, and the like, salts of dibasic carboxylic acids, for example, maleic acid, fumaric acid, and the like; and salts of tribasic carboxylic acids, such as carboxysuccinic acid, citric acid, and the like.

Effective quantities of the compounds of the invention can be administered orally, for example, with an inert diluent or with an edible carrier. They can be enclosed in gelatin capsules or compressed into tablets. For the purposes of oral therapeutic administration, compounds of the invention can be incorporated with an excipient and used in the form of tablets, troches, capsules, elixirs, suspensions, syrups, wafers, chewing gums, and the like. These preparations should contain at least 0.5% of active compound of the invention, but can be varied depending upon the particular form and can conveniently be between 4% to about 70% of the weight of the unit. The amount of active compound in such a composition is such that a suitable dosage will be obtained. Preferred compositions and preparations according to the present invention are prepared so that an oral dosage unit form contains between 1.0–300 milligrams of the active compound of the invention.

Tablets, pills, capsules, troches, and the like can also contain the following ingredients: a binder, such as microcrystalline cellulose, gum tragacanth, or gelatin; an excipient, such as starch or lactose, a disintegrating agent such as alginic acid, Primogel, corn starch, and the like; a lubricant such as magnesium stearate or Sterores; a glidant such as colloidal silicon dioxide; and a sweetening agent such as sucrose; or saccarin, or a flavoring agent, such as peppermint, methyl salicylate, or orange flavoring. When the dosage unit form is a capsule, it can contain, in addition to materials of the above type, a liquid carrier such as a fatty oil. Other dosage unit forms can contain various materials that modify the physical form of the dosage unit, for example, as coatings. Thus, tablets or pills can be coated with sugar, shellac, or other enteric coating agents. A syrup can contain, in addition to the active compounds, sucrose as a sweetening agent and certain perservatives, dyes, colorings, and flavors. Materials used in preparing these various compositions should be pharmaceutically pure and non-toxic in the amounts used.

For the purpose of parenteral therapeutic administrations, the active compound of the invention can be incorporated into a solution or suspension. These preparations should contain at least 0.1% of active compound, but can be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

Solutions or suspensions can also include the following components: a sterile diluent, such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates, and agents for the adjustment of tonicity such as sodium chloride or dextrose. The parenteral preparation can be enclosed in ampules, disposable syringes, or multiple dose vials made of glass or plastic.

The highly lipophilic esters, amides, carbonates and carbamates of the present invention are capable of sustained release in mammals for a period of several days or from about one to four weeks when formulated and administered as depot preparations, as for example, when injected in a properly selected pharmaceutically acceptable oil. The preferred oils are of vegetable origin such as sesame oil, cottonseed oil, corn oil, coconut oil, soybean oil, olive oil and the like, or they are synthetic esters of fatty acids and polyfunctional alcohols such as glycerol or propylene glycol.

The depot compositions of the present invention are prepared by dissolving or suspending a highly lipophilic ester, amide, carbonate or carbamate of the instant invention in a pharmaceutically acceptable oil under sterile conditions. The oil is selected so as to obtain a release of the active ingredient over a desired period of time. The appropriate oil may easily be determined by consulting the prior art, or without undue experimentation by one skilled in the art.

An appropriate dose of a compound in accordance with this embodiment of the invention is from about 0.01 to 10 mg/kg of body weight per injection. Preferably, the depot formulations of this invention are administered as unit dose preparations comprising about 0.5 to 5.0 ml of a 0.1 to 20% weight/weight solution of compound in the oil. It is to be understood that the doses set forth herein are exemplary only and that they do not, to any extent, limit the scope or practice of the invention.

Representative examples of compounds of the invention and of intermediates used in their synthesis are set forth in Table 5. The examples are for illustrative purposes only and are not to be construed as limiting the invention. All temperatures are given in degrees Centigrade (°C.) unless indicated otherwise.

TABLE 5

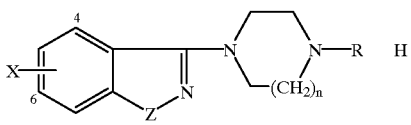

| Ex. # | X | n | R | HW | Z |
|---|---|---|---|---|---|
| 1b | 6-OCH$_3$ | 1 | 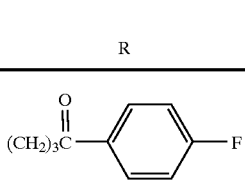 | — | O |
| 2 | 6-OH | 1 | 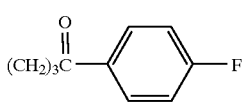 | — | O |

TABLE 5-continued

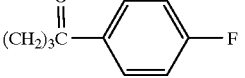

| Ex. # | X | n | R | HW | Z |
|---|---|---|---|---|---|
| 3 | 6-OH | 1 | (CH$_2$)$_3$C(=O)-C$_6$H$_4$-F | HBr | O |
| 4 | 6-OC(=O)O(CH$_2$)$_5$CH$_3$ | 1 | (CH$_2$)$_3$C(=O)-C$_6$H$_4$-F | — | O |
| 5 | 6-OC(=O)adamantyl | 1 | (CH$_2$)$_3$C(=O)-C$_6$H$_4$-F | — | O |
| 6 | 6-OC(=O)(CH$_2$)$_8$CH$_3$ | 1 | (CH$_2$)$_3$C(=O)-C$_6$H$_4$-F | — | O |
| 7 | 6-OC(=O)NH(CH$_2$)$_3$CH$_3$ | 1 | (CH$_2$)$_3$C(=O)-C$_6$H$_4$-F | — | O |
| 8 | 6-OCH$_3$ | 2 | H | — | O |
| 9c | 6-OCH$_3$ | 1 | (CH$_2$)$_3$C(=O)-C$_6$H$_4$-F | — | NH |
| 9e | 6-OH | 1 | (CH$_2$)$_3$C(=O)-C$_6$H$_4$-F | HCl | NCH$_3$ |

EXAMPLES

Example 1

3-[1-(4'-Fluorobenzoyl)propyl-4-piperazinyl]-6methoxy-1,2-benzisoxazole a. 6-Methoxy-3-(1-piperazinyl)-1,2-benzisoxazole hemihydrate A mixture of 3-chloro-6-methoxy-1,2-benzisoxazole (3.0 g) and piperazine (6.0 g) was heated to 140° C. over 4 hours in a sealed tube and then cooled to room temperature. The contents of the tube were dissolved in MeOH and further diluted with EtOAc (IL). The precipitate was filtered and the filtrate dried over MgSO$_4$ and concentrated in vacuo. Flash chromatography (silica gel) eluting with 30% MeOH/EtOAc provided a residue upon evaporation (3.6 g, m.p. 79–80 C.).

ANALYSIS: Calculated for C$_{12}$H$_{15}$N$_3$O$_2$·0.5H$_2$O: 59.490%C 6.65%H 17.34%N Found: 59.25%C 6.28%H 17.30%N b. 3-[1-(4'-Fluorobenzoyl)propyl-4-piperazinyl]-6-methoxy-1,2-benzisoxazole To a stirred solution of 6-methoxy-3-(1-piperazinyl)-1,2-benzisoxazole (5.0 g, 21.4 mmol) in acetonitrile (25 ml) was added K$_2$CO$_3$ (3.6 g, 25.7 mmol), KI (0.4 g, 2.1 mmol) and 4-chloro-4'-fluorobutyrophenone (5.2 g, 25.7 mmol) under N$_2$. The reaction was heated at reflux for 5 hours and allowed to cool to room temperature. The material was diluted with EtOAc, washed with water and brine, dried with MgSO$_4$, and concentrated in vacuo. The material was flashed chromatographed (silica gel) eluting with 3:2 EtOAc/heptane affording the pure free base of the product.

ANALYSIS: Calculated for C$_{22}$H$_{24}$N$_3$O$_3$F: 66.48%C 6.09%H 10.57%N Found: 66.32%C 6.00%H 10.45%N

Example 2

3-[1-(4'-Fluorobenzoyl)propyl-4-piperazinyl]-6hydroxy-1,2-benzisoxazole

A solution of 3-[1-(4'-fluorobenzoyl)propyl-4-piperazinyl]-6-methoxy-1,2-benzisoxazole (3.5 g, 8.8 mmol) and 48% hydrobromic acid was heated at 120° C. for 4 hours. The reaction was neutralized with saturated $Na_2CO_3$ solution, extracted with EtOAc, and the organic phase was dried ($MgSO_4$) and concentrated in vacuo. Flash column chromatography (silica gel) eluting with 5% MeOH/$CH_2Cl_2$, concentration of the desired fractions and recrystallization from EtOAc provided the product as an off-white solid (0.5 g, 15%, m.p. 181–182° C.).

ANALYSIS: Calculated for $C_{21}H_{22}N_3O_3F$: 65.78%C 5.78%H 10.96%N Found: 65.52%C 5.89%H 10.76%N

Example 3

3-[1-(4'-Fluorobenzoyl)propyl-4-piperazinyl]-6hydroxy-1,2-benzisoxazole hydrobromide A solution of ethereal hydrobromic acid was added to a solution of 3-[1-(4'-fluorobenzoyl)propyl-4-piperazinyl]-6-hydroxy-1,2-benzisoxazole (0.31 g, 0.8 mmol) in 50% $CH_3CN$/EtOAc and chilled to 0° C. for 1 hour. The precipitate was filtered under $N_2$ and dried in vacuo to afford the hydrobromide salt as a white solid (0.3 g, 81%, m.p. 260–261° C.).

ANALYSIS: Calculated for $C_{21}H_{22}N_3O_3F$ HBr: 54.32%C 4.990%H 9.05%N Found: 54.75%C 5.05%H 9.04%N

Example 4

Carbonic acid (3-[4-[4-(4-fluorophenyl)-4-oxo-butyl]-piperazin-1-yl]-1,2-benzisoxazol-6-yl)ester hexyl ester To a suspension of the compound of Example 3 (7.6 g, 16.4 mmol) in EtOAc (200 ml) was added $NaHCO_3$ (sat., 100 ml) at room temperature. After stirring over night, the solids were removed via filtration and the two-phase filtrate was transferred to a separatory funnel. The layers were separated and the organic phase was dried over $Na_2SO_4$. Filtration and concentration of the filtrate gave 2.9 g (47%) of the compound of Example 2.

This free amine (0.50 g, 1.31 mmol) was suspended in anhydrous THF (25 ml), under nitrogen, and treated with hexyl chloroformate (97%, 0.27 ml, 1.57 mmol). Milled potassium carbonate (0.22 g, 1.57 mmol) was then added and the reaction mixture was allowed to stir for eighteen hours. The solids were removed via filtration and washed with DCM. The combined filtrates were concentrated to give the crude product which was purified via flash column chromatography (silica gel, ethyl acetate). Concentration of the desired fractions gave 0.51 g (76%) of the product as a light brown solid, m.p. 77–80° C.

ANALYSIS: Calculated for $C_{28}H_{34}FN_3O_5$: 65.74%C 6.70%H 8.21%N Found: 65.80%C 6.74%H 8.04%N

Example 5

Adamantane-1-carboxylic acid 3-[4-[4-(4-fluorophenyl)-4-oxo-butyl]-piperazin-1-yl]-1,2-benzisoxazol-6-yl ester The compound of Example 2 (0.50 g, 1.31 mmol) was suspended in acetonitrile (15 ml), under nitrogen, and treated with $K_2CO_3$ (0.20 g, 1.44 mmol). 1-Adamantanecarbonyl chloride (0.30 g, 1.44 mmol) was then added and the reaction mixture was allowed to stir for sixty hours. The solids were removed via filtration and washed with DCM. The combined filtrates were concentrated to give the crude product which was purified via flash column chromatography (silica gel, ethyl acetate). Concentration of the desired fractions gave 0.52 g (73%) of the product as a white solid, m.p. 157–158° C.

ANALYSIS: Calculated for $C_{32}H_{36}FN_3O_4$: 70.44%C 6.65%H 7.70%N Found: 70.29%C 6.62%H 7.54%N

Example 6

Decanoic acid 3-[4-[4-(4-fluorophenyl)-4-oxo-butyl]-piperazin-1-yl]-1,2-benzisoxazol-6-yl ester The compound of Example 2 (0.60 g, 1.57 mmol) was suspended in acetonitrile (15 ml), under nitrogen, and treated with $K_2CO_3$ (0.24 g, 1.73 mmol). Decanoyl chloride (0.36 ml, 1.73 mmol) was then added and the reaction mixture was allowed to stir for sixty hours. The solids were removed via filtration and washed with DCM. The combined filtrates were concentrated to give 0.80 g (95%) of the desired product as a brown solid, m.p. 69–71° C.

ANALYSIS: Calculated for $C_{31}H_{40}FN_3O_4$ 69.25%C 7.50%H 7.82%N Found: 69.28%C 7.71%H 7.76%N

Example 7

Butyl carbamic acid 3-[4-[4-(4-fluorophenyl)-4-oxo-butyl]-piperazin-1-yl]- 1,2-benzisoxazol-6-yl ester The compound of Example 2 (0.50 g, 1.31 mmol) was suspended in anhydrous THF (25 ml), under nitrogen, and treated with butyl isocyanate (0.18 ml, 1.57 mmol). Milled potassium carbonate (0.22 g, 1.57 mmol) was then added and the reaction mixture was allowed to stir for eighteen hours. The solids were removed via filtration and washed with DCM. The combined filtrates were concentrated to give the crude product which was purified via flash column chromatography (silica gel, ethyl acetate). Concentration of the desired fractions gave 0.40 g (63%) of the product as a light brown solid, m.p. 137–141° C.

ANALYSIS: Calculated for $C_{26}H_{31}FN_4O_4$: 64.72%C 6.48%H 11.61%N Found: 64.29%C 6.83%H 11.77%N

Example 8

3-(1-homopiperazinyl)-6-methoxy-1,2-benzisoxazole

3-Chloro-6-methoxy-1,2-benzisoxazole (5.0 g, 27.2 mmol) and homopiperazine (8.2 g, 81.6 mmol) were combined and mechanically stirred under $N_2$ at 140° C. for 45 minutes. The reaction mixture was cooled to room temperature, dissolved with EtOAc (500 ml), and the solution was washed with water, brine, dried over $MgSO_4$, and concentrated in vacuo. Flash column chromatography (silica gel, 20% MeOH/$CH_2Cl_2$) provided the product (2.0 g, m.p. 74–75° C.

ANALYSIS: Calculated for $C_{13}H_{17}N_3O_2$: 63.14%C 6.93%H 16.99%N Found: 62.88%C 6.85%H 16.81%N

Example 9

1-(4Fluorophenyl)-4-[4-[6-hydroxy-1-methyl-1H-indazol-3-yl]-piperazin-1-yl]-butan-1-one hydrochloride hydrate a. 4-[4-[N-(p-Toluenesulfonylhydazono)-2-fluoro-4-methoxyphenylmethyl]-piperazin-1-yl]-1-(4-fluorophenyl)butan-1-one To a stirred solution of alpha-chloro-2-fluoro4-methoxy benzaldehyde, 1-p-toluenesulfonylhydrazone (4.6 g, 12.8 mmol) in chloroform (20 ml) was added a solution of 1-(4-fluorophenyl)4-piperazin-1-yl-butan-1-one (3.2 g, 12.8 mmol) in chloroform (20 ml) and allowed to stir at ambient temperature under nitrogen for 1 hour. The reaction was diluted with methylene chloride, washed with water, dried over $Na_2SO_4$, and concentrated in vacuo. The residue was flash chromatographed eluting with 3:2 $CH_2Cl_2$/EtOAc to afford the product, 2.5 g, mp=66–67 C.

ANALYSIS: Calculated for $C_{29}H_{32}N_4O_4F_2S$: 61.04%C 5.65%H 9.82%N Found: 60.74%C 5.53%H 9.69%N b. 1-(4-Fluorophenyl)-4-[4-[6-methoxy-1-toluene-4-sulfonyl)-1H-indazol-3-yl]-piperazin-1-yl]-butan-1-one To a stirred solution of the compound of Example 9a (2.5 g, 4.4 mmol) in N,N-dimethylformamide (10 ml) was added $K_2CO_3$ (1.2 g, 8.8 mmol) under $N_2$. The reaction was heated to 90 C. for 3 hours. The reaction mixture was then cooled, diluted with with ethyl acetate, washed with brine (6 times), dried over $Na_2SO_4$, and concentrated in vacuo. The residue was flash chromatographed eluting with 3:2 $CH_2Cl_2$/EtOAc to afford the product, 2.3 g, mp=120–121 C.

ANALYSIS Calculated for $C_{29}H_{31}N_4O_4FS$: 63.26%C 5.67%H 10. 17%N Found: 62.99%C 5.71%H 9.86%N c. 1(4-Fluorophenyl)-4-[4-[6-methoxy)-1H-indazol-3-yl]-piperazin-1-yl]-butan-1-one A mixture of the compound of Example 9b (1 g, 1.8 mmol) and 30 ml of 12 M hydrochloric acid was heated at 90 C for 1 hour under nitrogen. The reaction mixture was cooled, diluted with EtOAc, and neutralized with $Na_2CO_3$ (sat'd). The organic layer was separated and the aqueous layer was extracted again with EtOAc. The organic layers were combined, dried over $Na_2SO_4$ and evaporated to afford 0.65 g of the desired product, mp=157–162 C.

d. 1-(4-Fluorophenyl)-4-[4-[6-methoxy)-1-methyl-1H-indazol-3-yl]-piperazin-1-yl]-butan-1-one To a mixture of the compound of Example 9c (0.45 g, 1.13 mmol) and potassium hydroxide (0.19 g, 3.4 mmol) in 40 ml of acetone, there was added dimethylsulfate (0.14 g, 0.11 ml, 1.13 mmol) and the mixture was refluxed for three hours. The reaction mixture was cooled, diluted with methylene chloride and washed with brine. The organic layer was dried over $Na_2SO_4$ and concentrated in vacuo. The residue was flash chromatographed. Elution with 5% MeOH/$CH_2Cl_2$ gave 0.4 g of the product, mp=103–104 C.

e. 1-(4-Fluorophenyl)-4-[4-[6-hydroxy)-1-methyl-1H-indazol-3-yl]-piperazin-1-yl]-butan-1-one hydrochloride hydrate To 48% hydrobromic acid (20 ml) was added the compound of Example 9d (0.40 g, 1.0 mmol) and the mixture was heated to 110° C. under N2 for four (4) hours. Then the mixture was cooled and diluted with EtOAc and neutralized with saturated Na2CO3 solution and extracted with additional EtOAc. The organic layers were combined, dried over Na2SO4 and concentrated in vacuo. The residue was flash chromatographed (silica gel, 3% MeOH/CH2Cl2 to yield a white solid which was dissolved in EtOAc and acidified with ethereal hydrochloride acid to afford the salt, 0.30 g, mp=243–244° C.

ANALYSIS Calculated for $C_{22}H_{25}N_4O_2F.HCl.H_2O$: 58.60%C 6.26%H 12.40%N Found: 58.60%C 6.06%H 12.36%N It should be understood that this specification and examples are set forth by way of illustration and not limitation and that various modifications and changes may be made without departing from the spirit and scope of the present invention as defined by the appended claims.

We claim:

1. A compound of the formula

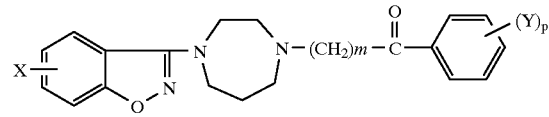

wherein

X is —OH, OC(=O)($C_1$–$C_{18}$)alkyl, —OC(=O)NH ($C_1$–$C_{18}$)alkyl, —OC(=O)O($C_1$–$C_{18}$)alkyl or —OC(=O)—($C_3$–$C_{12}$)cycloalkyl;

Y is hydrogen, halogen, trifluoromethyl, ($C_1$–$C_6$)alkoxy, cyano or nitro;

m is 1, 2, 3, or 4; and p is 1 or 2;

or the pharmaceutically acceptable addition salts thereof.

2. The compound of claim 1 of the formula:

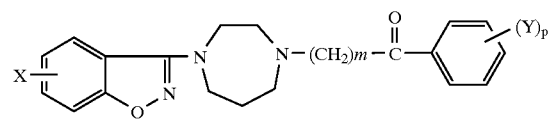

wherein

X is —OH, OC(=O)($C_1$–$C_{18}$)alkyl, —OC(=O)NH ($C_1$–$C_{18}$)alkyl, —OC(=O)O($C_1$–$C_{18}$)alkyl or —OC(=O)—($C_3$–$C_{12}$)cycloalkyl;

Y is hydrogen or halogen m is 1, 2, 3, or 4; and p is 1 or the pharmaceutically acceptable addition salts thereof.

3. The compound of claim 2 wherein m is 3 and Y is 4-fluoro.

4. The compound of claim 3 wherein X is 6-hydroxy, 6-OC(=O)NHbutyl, 6-OC(=O)Ohexyl, 6-OC(=O)nonyl, or 6-OC(=O)adamantyl; and its pharmaceutically acceptable acid addition salts.

5. A process for preparing a compound of the formula:

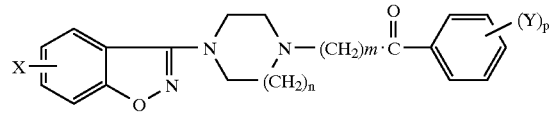

wherein

X is —OH, OC(=O)($C_1$–$C_{18}$)alkyl, —OC(=O) ($C_6$–$C_{12}$)aryl, —OC(=O)($C_6$–$C_2$)alkyl($C_6$–$C_{10}$)aryl, OC(=O)NH($C_1$–$C_{18}$)alkyl, —OC(=O)($C_3$–$C_{12}$)alkyl ($C_3$–$C_8$)cycloakyl, —OC(=O)O($C_1$–$C_{18}$)alkyl or —OC(=O)—($C_3$–$C_{12}$)cycloalkyl;

Y is H, halogen, trifluoromethyl, ($C_1$–$C_6$)alkoxy, cyano or nitro;

m is 1, 2, 3, or 4;

n is 1 or 2; and p is 1 or 2; or the pharmaceutically acceptable addition salts thereof comprising reacting a compound of the formula:

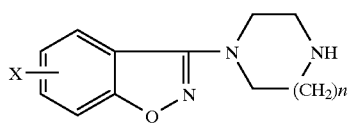

wherein X and n are defined as above, with a compound of the formula:

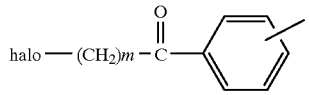

wherein halo is Br or Cl, and Y, m and p are defined as above, in a polar non-protic organic solvent in the presence of a base and a catalyst.

6. A process for preparing a compound of the formula:

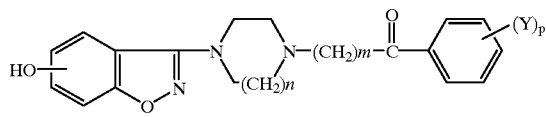

wherein
Y is H, halogen, trifluoromethyl, $(C_1-C_6)$alkoxy, cyano or nitro;
m is 1, 2, 3 or 4;
n is 1 or 2; and
p is 1 or 2; or the pharmaceutically acceptable acid addition salts thereof, comprising heating a compound of the formula:

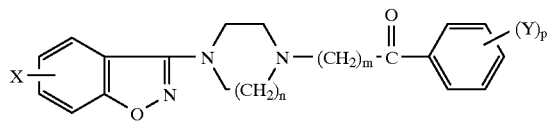

wherein X is —OC(=O)$(C_1-C_{18})$alkyl, —OC(=O)$(C_6-C_{10})$aryl, —OC(=O)$(C_1-C_{12})$alkyl$(C_6-C_{10})$aryl, —OC(=O)NH$(C_1-C_{18})$alkyl, —OC(=O)$(C_1-C_{12})$alkyl$(C_3-C_8)$cycloalkyl, —OC(=O)O$(C_1-C_{18})$alkyl, or —OC(=O)—$(C_3-C_{12})$cycloalkyl, and Y, m, n and p are defined as above, with 48% HBr.

7. A method of treating psychosis in a mammal in need of psychosis treatment which comprises administering to such a mammal a psychosis treating effective amount of a compound of claim 1.

8. A psychosis treating pharmaceutical composition comprising an adjuvant and as the active ingredient, a psychosis treating effective amount of a compound of claim 1.

9. A method of providing an anti-psychotic effect of from about one to four weeks which comprises administering to a mammal a composition according to claim 8 wherein the effective amount of the composition is sufficient to produce an anti-psychotic effect of from about one to four weeks.

10. A depot pharmaceutical composition for treating psychosis comprising an adjuvant and as the active ingredient, a psychosis effective amount of a compound of the formula

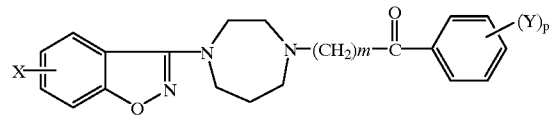

wherein

X is —OC(=O)$(C_1-C_{18})$alkyl, —OC(=O)NH$(C_1-C_{18})$alkyl, —OC(=O)O$(C_1-C_{18})$alkyl or —OC(=O)—$(C_3-C_{12})$cycloalkyl;

Y is hydrogen or halogen m is 1, 2, 3, or 4; and p is 1; or the pharmaceutically acceptable addition salts thereof.

* * * * *

UNITED STATES PATENT AND TRADEMARK OFFICE
CERTIFICATE OF CORRECTION

PATENT NO. : 5,965,554

DATED : October 12, 1999

INVENTOR(s) : Mark G. Palermo, Lawrence L. Martin, Peter A. Nemoto

It is certified that error appears in the above-identified patent and that said Letters Patent is hereby corrected as shown below:

<u>Column 23, line 12</u>

The formula should read 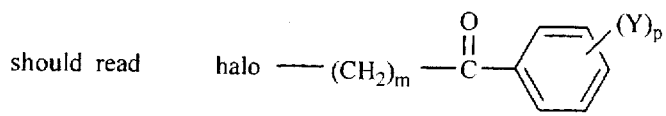

Signed and Sealed this

Twenty-first Day of March, 2000

Q. TODD DICKINSON

Attest:

*Attesting Officer*　　　*Commissioner of Patents and Trademarks*